United States Patent [19]

Kanemura et al.

[11] Patent Number: 5,352,758

[45] Date of Patent: Oct. 4, 1994

[54] MERCAPTO COMPOUND, ITS PREPARATION PROCESS, AND SULFUR-CONTAINING URETHANE RESINS AND LENSES USING THE SAME

[75] Inventors: Yoshinobu Kanemura; Katsuyoshi Sasagawa, both of Yokohama; Seiichi Kobayashi, Kamakura, all of Japan

[73] Assignee: Mitsui Toatsu Chemicals, Incorporated, Tokyo, Japan

[21] Appl. No.: 169,708

[22] Filed: Dec. 20, 1993

Related U.S. Application Data

[62] Division of Ser. No. 924,454, Aug. 4, 1992, Pat. No. 5,283,312.

[30] Foreign Application Priority Data

Aug. 8, 1991 [JP] Japan .................... 3-199278

[51] Int. Cl.$^5$ .................... C07C 319/06; C08G 18/08
[52] U.S. Cl. .................... 528/85; 528/60; 568/38; 568/57; 568/66; 568/69; 359/642
[58] Field of Search .................... 528/85, 60; 568/38, 568/57, 66, 69; 359/642

[56] References Cited

U.S. PATENT DOCUMENTS

| | | | |
|---|---|---|---|
| 3,544,543 | 12/1970 | Greco et al. | 568/50 |
| 4,355,185 | 10/1982 | Bergthaller et al. | 568/50 |
| 5,087,758 | 2/1992 | Kanemura et al. | 568/57 |

FOREIGN PATENT DOCUMENTS

| | | |
|---|---|---|
| 330363 | 8/1989 | European Pat. Off. |
| 378895 | 7/1990 | European Pat. Off. |
| 384725 | 8/1990 | European Pat. Off. |

*Primary Examiner*—John Kight, III
*Assistant Examiner*—John M. Cooney, Jr.
*Attorney, Agent, or Firm*—Burns, Doane, Swecker & Mathis

[57] ABSTRACT

A mercapto compound represented by the following formula (1):

$$HSCH_2CHCH_2SH \quad (1)$$
$$| $$
$$SCH_2CH_2SH$$

is obtained by reacting, in the presence of a mineral acid, thiourea with a compound represented by the following formula (2):

$$X-CH_2CHCH_2SCH_2CH_2OH \quad (2)$$
$$|$$
$$OH$$

wherein X means a hydroxyl group or a chlorine or bromine atom, and then adding a base to alkalinize the reaction mixture so that the reaction product is hydrolyzed.

The mercapto compound represented by the formula (1) can be reacted with at least one cyanate compound selected from the group consisting of polyisocyanate compounds, polyisothiocyanate compounds and isocyanate-group-containing isothiocyanate compounds to form a sulfur-containing urethane resin. A lens made of the resin is colorless and transparent, has high refractive index and low dispersion characteristics, and is excellent especially in heat resistance.

8 Claims, No Drawings

MERCAPTO COMPOUND, ITS PREPARATION PROCESS, AND SULFUR-CONTAINING URETHANE RESINS AND LENSES USING THE SAME

This application is a divisional of U.S. application Ser. No. 07/924,454, filed Aug. 4, 1992, now U.S. Pat. No. 5,283,312.

BACKGROUND OF THE INVENTION

1) Field of the Invention

This invention relates to a novel mercapto compound and its preparation process, sulfur-containing urethane resins using the mercapto compound and lenses made of the resins.

The mercapto compound according to the present invention has a variety of utilities, for examples, as a crosslinking agent, epoxy resin hardener, curing agent, polymerization regulator, synthetic resin raw material, antioxidant, metal complex former, biochemical reagent and lubricant additive.

2) Description of the Related Art

Plastic lenses are lightweight and fragmentation-resistant compared with inorganic lenses and, moreover, are dyeable, so that they are finding rapidly increasing utility as optical elements, such as eyeglass lenses and camera lenses, in recent years.

Resins widely employed these days for such purposes include the resin available by radical polymerization of diethylene glycol bis(allylcarbonate) (hereinafter called "D.A.C."). This resin has various advantages such as excellent impact resistance, lightweight, superb dyeability, and good workability such as good cutting and grinding machinability.

The refractive index of a D.A.C. lens, however, is 1.50 ($n_D = 1.50$) which is lower than the refractive index ($n_D = 1.52$) of an inorganic lens. To obtain optical characteristics comparable with those of a glass lens, it is necessary to increase the central thickness, peripheral thickness and curvature of the D.A.C. lens, unavoidably resulting in an overall large thickness. There is accordingly an outstanding desire for the development of a lens resin having a still higher refractive index. Known examples of lens resins which can provide a high refractive index include polyurethane resins available by reacting an isocyanate compound with a hydroxyl compound such as diethylene glycol (U.S. Pat. No. 4,443,588), a halogen-containing hydroxyl compound such as tetrabromobisphenol A (Japanese Patent Laid-Open No. 164615/1983) or a hydroxyl compound having the diphenyl sulfide skeleton (Japanese Patent Laid-Open No. 194401/1985).

Although lenses made of these known resins have a refractive index improved over lenses made of D.A.C., they are accompanied by the drawback(s) that they may be insufficient in refractive index and/or they may be poor in weatherability and/or high in specific gravity due to the use of a compound containing many halogen atoms or an aromatic ring in the molecule thereof with a view toward imparting an improved refractive index.

The present assignee has already filed an application for patent on 1,2-bis[(2-mercaptoethyl)thio]-3-mercaptopropane (U.S. Pat. No. 5,087,758). When this compound is polymerized with m-xylylene diisocyanate employed most widely for the production of a lens resin, the withstandable maximum temperature of the resulting resin is 98° C. A lens made of this resin is therefore deformed at temperature conditions (90°–95° C.) under which plastic lenses are usually dyed, leading to the desire for further improvements in heat resistance.

In addition, the color hue upon polymerization is important. The raw material of the plastic lens requires that its vapor pressure is not too high to permit ready distillation for its purification on an industrial scale. From this viewpoint too, it has been desired to develop a mercapto compound having a molecular weight of about 200.

SUMMARY OF THE INVENTION

An object of this invention is to provide a novel mercapto compound which can satisfy the above-described requirements.

Another object of this invention is to provide a novel, sulfur-containing urethane resin available from the use of the mercapto compound so obtained.

A further object of this invention is to provide a plastic lens having good heat resistance.

With the foregoing circumstances in view, the present inventors have proceeded with a further investigation. As a result, the present inventors have found a novel mercapto compound, leading to the completion of the present invention.

The present invention therefore provides a mercapto compound represented by the following formula (1):

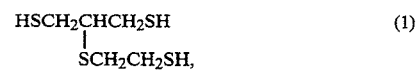

(1)

a sulfur-containing urethane resin making use of the mercapto compound, and also a lens made of the resin. Described more specifically, the present invention provides a mercapto compound having a molecular weight of about 200 thereby to permit ready distillation for its purification and having only a low level of a sulfur odor and being colorless and transparent, sulfur-containing urethane resin and lens obtained from the mercapto compound and having high refractive index and low dispersion characteristics, light weight, and excellent weatherability, impact resistance and heat resistance, as well as their preparation, production and fabrication processes.

DETAILED DESCRIPTION OF THE PREFERRED EMBODIMENTS

To prepare the mercapto compound of the formula (1) of the present invention, a glycerin derivative such as 1-chloro-2,3-propanediol or 1-bromo-2,3propanediol, an epihalohydrin such as epichlorohydrin or epibromohydrin, or glycidol and 2-mercaptoethanol are reacted in the presence of an alkali under cooling or heating, thereby obtaining a compound represented by the following formula (2):

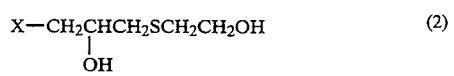

(2)

wherein X means a hydroxyl group or a chlorine or bromine atom. After thiourea is reacted to the compound (2) in a mineral acid, the reaction product is subjected to hydrolysis under alkaline conditions. At the same time, rearrangement takes place at the 1- and 2-positions so that the mercapto compound of the formula (1) is obtained.

Described specifically, 2-mercaptoethanol and an alkali catalyst are dissolved in water, followed by the dropwise addition of a glycerin derivative, epihalohydrin or glycidol. It is preferred to react them at 0°–120° C.

It is necessary to use 2-mercaptoethanol in an amount at least 1 equivalent, preferably 1.0–1.2 equivalents relative to the glycerin derivative, epihalohydrin or glycidol.

Examples of the alkali catalyst include metal hydroxides such as sodium hydroxide and potassium hydroxide, metal carbonates such as sodium carbonate and potassium carbonate, and tertiary amines such as triethylamine and tributylamine.

To the thus-obtained compound represented by the formula (2), thiourea is reacted in an amount of at least 3 equivalents, preferably 3–6 equivalents relative to the compound (2) at a temperature ranging from room temperature to the reflux temperature, in at least 3 equivalents, preferably 3–12 equivalents of an aqueous solution of a mineral acid. Usable examples of the mineral acid include hydrochloric acid, hydrobromic acid, hydroiodic acid, sulfuric acid and phosphoric acid. Hydrochloric acid is preferred because a sufficient reaction velocity is available and coloration of the reaction product can be controlled.

The hydrolytic reaction, which is supposed to be conducted next, is effected at a temperature ranging from room temperature to a reflux temperature after adding at least 3 equivalents, preferably 3–12 equivalents of a metal hydroxide such as sodium hydroxide or potassium hydroxide, ammonia or an amine such as triethylamine to the reaction mixture to alkalinize the reaction mixture. The temperature at the time of addition of the base is preferably 0°–50° C. Temperatures higher than 50° C. tend to result in coloration of the reaction product.

The thus-prepared mercapto compound represented by the formula (1) can be purified by the general procedures that, subsequent to its extraction with an organic solvent such as toluene, the extract is subjected to acid washing, water washing, concentration and filtration.

The molecular weight of the mercapto compound of this invention is 200 so that its purification by distillation is easy. Specifically, its boiling point is 135°–140° C. at 0.25 mmHg so that its distillation and purification can be effected with ease on an industrial scale.

1,2,3-Tris[(2-mercaptoethyl)thio]propane which has a similar structure to the mercapto compound of this invention has a boiling point of 200° C. or higher under similar pressure and tends to undergo a decomposition reaction, and the resulting fraction is colored. A low pressure of 1 mmHg or lower is therefore required. It is, however, difficult realize such a low pressure industrially. On the other hand, 1,2,3-trimercaptopropane whose molecular weight is smaller has a boiling point lower than the mercapto compound according to this invention provided that the degree of depressurization is the same. Its molecular weight is small, namely, 140, resulting in the drawback that its vapor pressure is high and unpleasant sulfur odor is strong.

Although the above series of reactions in this invention can be practiced in the surrounding environment, it is preferred to conduct it under nitrogen.

The sulfur-containing urethane resin according to this invention is obtained by reacting the mercapto compound represented by the formula (1) with at least one cyanate compound selected from polyisocyanate compounds, polyisothiocyanate compounds and isocyanate-group-containing polyisothiocyanate compounds.

Illustrative polyisocyanate compounds usable as raw materials for the sulfur-containing urethane resin in this invention include aliphatic polyisocyanates such as ethylene diisocyanate, trimethylene diisocyanate, tetramethylene diisocyanate, hexamethylene diisocyanate, octamethylene diisocyanate, nonamethylene diisocyanate, 2,2'-dimethylpentane diisocyanate, 2,2,4-trimethylhexane diisocyanate, decamethylene diisocyanate, butene diisocyanate, 1,3-butadiene-1,4-diisocyanate, 2,4,4-trimethylhexamethylene diisocyanate, 1,6,11-undecane triisocyanate, 1,3,6-hexamethylene triisocyanate, 1,8-diisocyanato-4-isocyanato methyloctane, 2,5,7-trimethyl-1,8-diisocyanato-5-isocyanato methyloctane, bis(isocyanatoethyl) carbonate, bis(isocyanatoethyl) ether, 1,4-butylene glycol dipropyl ether-w,w'-diisocyanate, lysinediisocyanatomethyl ester, lysine triisocyanate, 2-isocyanatoethyl-2,6-diisocyanatohexanoate, 2-isocyanatopropyl-2,6-diisocyanatohexanoate, xylylene diisocyanate, bis(isocyanatoethyl)benzene, bis(isocyanatopropyl)benzene, α,α,α',α'-tetramethylxylylene diisocyanate, bis(isocyanatobutyl)benzene, bis(isocyanatomethyl)naphthalene, bis(isocyanatomethyl)diphenyl ether, bis(isocyanatoethyl) phthalate, mesitylylene triisocyanate and 2,6-di(isocyanatomethyl)furan; alicyclic polyisocyanates such as isophorone diisocyanate, bis(isocyanatomethyl)cyclohexane, dicyclohexylmethane diisocyanate, cyclohexane diisocyanate, methylcyclohexane diisocyanate, dicyclohexyldimethylmethane diisocyanate, 2,2'-dimethyldicyclohexylmethane diisocyanate, bis(4-isocyanato-n-butylidene)pentaerythritol, dimeric acid diisocyanate, 2-isocyanatomethyl-3-(3-isocyanatopropyl)-5-isocyanatomethylbicyclo-[2.2.1]-heptane, 2-isocyanatomethyl-3-(3-isocyanatopropyl)-6-isocyanatomethyl-bicyclo-[2.2.1]heptane, 2-isocyanatomethyl-2-(3-isocyanatopropyl)-5-isocyanatomethyl-bicyclo-[2.2.1]-heptane, 2-isocyanato-methyl-2-(3-isocyanatopropyl)-6-isocyanatomethyl-bicyclo-[2,2.1]-heptane, 2-isocyanatomethyl-3-(3-isocyanatopropyl)-5-(2-isocyanatoethyl)-bicyclo-[2.2.1]-heptane, 2-isocyanatomethyl-3-(3-isocyanato-propyl)-6-(2-isocyanatoethyl)-bicyclo[2.2.1]-heptane, 2-isocyanatomethyl-2-(3-isocyanatopropyl)-5-(2-isocyanatoethyl)-bicyclo-[2.2.1]-heptane and 2-isocyanatomethyl-2-(3-isocyanatopropyl)-6-(2-isocyanatoethyl)-bicyclo-[2.2.1]-heptane; aromatic polyisocyanates such as phenylene diisocyanate, tolylene diisocyanate, ethylphenylene diisocyanate, isopropylphenylene diisocyanate, dimethylphenylene diisocyanate, diethylphenylene diisocyanate, diisopropylphenylene diisocyanate, trimethylbenzene triisocyanate, benzene triisocyanate, naphthalene diisocyanate, methylnaphthalene diisocyanate, biphenyl diisocyanate, toluidine diisocyanate, 4,4'-diphenylmethane diisocyanate, 3,3'-dimethyldiphenylmethane-4,4'-diisocyanate, bibenzyl-4,4'-diisocyanate, bis(isocyanatophenyl)ethylene, 3,3'-dimethoxybiphenyl-4,4'-diisocyanate, triphenylmethane triisocyanate, polymeric MDI, naphthalene triisocyanate, diphenylmethane-2,4,4'-triisocyanate, 3-methyldiphenylmethane-4,6,4'-triisocyanate, 4-methyldiphenylmethane-3,5,2',4',6'-pentaisocyanate, phenylisocyanatomethylisocyanate, phenylisocyanatoethylisocyanate, tetrahydronaphthylene diisocyanate, hexahydrobenzene diisocyanate, hexahydrodiphenylmethane-4,4'-diisocyanate, diphenyl ether diisocyanate, ethylene glycol diphenyl ether diisocyanate, 1,3-propylene glycol diphenyl ether diisocyanate, benzophenone diisocyanate, diethylene glycol diphenyl ether diisocyanate, dibenzofuran diisocyanate, carbazole diisocyanate, ethylcarbazole diisocyanate and dichlorocarbazole diisocyanate; sulfur-containing aliphatic polyisocyanates such as thiodiethyl diisocyanate, thiodipropyl diisocyanate, thiodihexyl diisocyanate, dimethylsulfone diisocyanates, dithiodimethyl diisocyanate, dithiodiethyl diisocyanate and dithiodipropyl diisocyanate; aromatic sulfide polyisocyanate such as diphenyl sulfide-2,4'-diisocyanate, diphenyl sulfide-4,4'-diisocyanate, 3,3'-dimethoxy-4,4'-diisocyanatodibenzyl thioether, bis(4-isocyanatomethylbenzene) sulfide and 4,4'-methoxybenzenethioethyleneglycol-3,3'-diisocyanate; aromatic disulfide polyisocyanates such as diphenyldisulfide-4,4'-diisocyanate, 2,2'-dimethyldiphenyldisulfide-5,5'-diisocyanate, 3,3'-dimethyldiphenyldisulfide-5,5,-diisocyanate, 3,3'-dimethyldiphenyldisulfide-6,6'-diisocyanate, 4,4'-dimethyldiphenyldisulfide-5,5'-diisocyanate, 3,3'-dimethoxydiphenyldisulfide-4,4'-diisocyanate and 4,4'-dimethoxydiphenyldisulfide-3,3'-diisocyanate; aromatic sulfone polyisocyanates such as diphenylsulfone-4,4'-diisocyanate, diphenylsulfone-3,3'-diisocyanate, benzidinesulfone-4,4'-diisocyanate, diphenylmethanesulfone-4,4'-diisocyanate, 4-methyldiphenylsulfone-2,4'-diisocyanate, 4,4'-dimethoxydiphenylsulfone-3,3'-diisocyanate, 3,3'-dimethoxy-4,4'-diisocyanatodibenzylsulfone, 4,4'-dimethyldiphenylsulfone-3,3'-diisocyanate, 4,4'-di-tert-butyldiphenylsulfone-3,3'-diisocyanate, 4,4'-methoxybenzeneethylenedisulfone-3,3'-diisocyanate and 4,4'-dichlorodiphenylsulfone-3,3'-diisocyanate; and sulfonic acid ester polyisocyanates such as 4-methyl-3-isocyanatobenzenesulfonyl-4'-isocyanatophenol ester and 4-methoxy-3 isocyanatobenzenesulfonyl-4'-isocyanatophenol ester; aromatic sulfonamides such as 4-methyl-3-isocyanatobenzenesulfonylanilido-3'-methyl-4'-isocyanate, dibenzenesulfonyl-ethylenediamine-4,4'-diisocyanate, 4,4'-methoxybenzenesulfonylethylenediamine-3,3,diisocyanate and 4-methyl-3-isocyanatobenzenesulfonylanilido-4-methyl-3'-isocyanate; sulfur-containing heterocyclic compounds such as thiophene-2,5-diisocyanate; and 1,4-dithiane-2,5-diisocyanate.

Also usable are their halogen-substituted derivatives such as chlorine-substituted derivatives and bromine-substituted derivatives, alkyl-substituted derivatives, alkoxyl-substituted derivatives, nitrosubstituted derivatives, prepolymer-type derivatives modified with polyhydric alcohols, carbodiimidemodified derivatives, urea-modified derivatives, biuret-modified derivatives, dimerized reaction products, trimerized reaction products, and the like.

The polyisothiocyanate compound employed as a raw material for the sulfur-containing urethane resin in this invention is a compound containing two or more —NCS groups in a molecule and, optionally, one or more sulfur atoms in addition to the isothiocyanate groups. Specific examples include aliphatic polyisothiocyanates such as 1,2-diisothiocyanatoethane, 1,3-diisothiocyanatopropane, 1,4-diisothiocyanatobutane, 1,6-diisothiocyanatohexane thiocyanatohexane and p-phenylenediisopropylidene diisothiocyanate; alicyclic polyisothiocyanates such as cyclohexane diisothiocyanate; aromatic polyisothiocyanates such as 1,2-diisothiocyanatobenzene, 1,3diisothiocyanatobenzene, 1,4-diisothiocyanatobenzene, 2,4-diisothiocyanatotoluene, 2,5-diisothiocyanato-mxylene, 4,4'-diisothiocyanato-1,1'-biphenyl, 1,1'-methylenebis(4-isothiocyanatobenzene), 1,1'-methylenebis(4-isothiocyanato-2-methylbenzene), 1,1'-methylenebis(4-isothiocyanato-3-methylbenzene), 1,1'-(1,2ethanediyl)bis(4-isothiocyanatobenzene), 4,4'-diisothiocyanatobenzophenone, 4,4'-diisothiocyanato-3,3'-dimethylbenzophenone, benzanilido-3,4'-diisothiocyanate, diphenyl ether-4,4'-diisothiocyanate and diphenylamine-4,4'-diisothiocyanate; heterocyclic-ring-containing isothiocyanates such as 2,4,6-triisothiocyanato-1,3,5-triazine; carbonyl isothiocyanates such as hexanedioyl diisothiocyanate, nonanedioyl diisothiocyanate, carbonic diisothiocyanate, 1,3-benzenedicarbonyl diisothiocyanate, 1,4-benzenedicarbonyl diisothiocyanate and (2,2'-bipyridine)-4,4'-dicarbonyl diisocyanate.

Illustrative bifunctional or higher polyisothiocyanates, which contain one or more sulfur atoms in addition to at least one isothiocyanato group and are usable as raw materials for the sulfur-containing urethane resin in the present invention, include sulfur-containing isothiocyanates such as thiobis(3-isothiocyanatopropane), thiobis(2-isocyanatoethane) and dithiobis(2-isothiocyanatoethane); sulfur-containing aromatic isothiocyanates such as 1-isothiocyanato-4[(2-isothiocyanato)sulfonyl]benzene, thiobis(4-isothiocyanatobenzene), sulfonylbis(4-isothiocyanatobenzene), sulfinylbis(4-isothiocyanatobenzene), dithiobis(4-isothiocyanatobenzene), 4-isothiocyanato-1-[(4-isothiocyanatophenyl)sulfonyl]-2-methoxybenzene, 4-methyl-3-isothiocyanatobenzenesulfonyl-4'-isothiocyanate phenyl ester, and 4-methyl-3-isothiocyanatobenzenesulfonylanilido-3'-methyl-4'-isothiocyanate; and sulfur-containing heterocyclic compounds such as thiophenone-2,5-diisothiocyanate and 1,4-dithiane-2,5-diisothiocyanate.

Also usable are their halogen-substituted derivatives such as chlorine-substituted derivatives and bromine-substituted derivatives, alkyl-substituted derivatives, alkoxyl-substituted derivatives, nitrosubstituted derivatives, prepolymer-type derivatives modified with polyhydric alcohols, carbodiimidemodified derivatives, urea-modified derivatives, biuret-modified derivatives, dimerized reaction products, trimerized reaction products, and the like.

Exemplary isothiocyanate compounds, which contain an isocyanato group and are usable as raw materials for the sulfur-containing urethane resin in this invention, include aliphatic or alicyclic compounds such as 1-isocyanato-3-isothiocyanatopropane, 1-isocyanato-5isothiocyanatopentane, 1-isocyanato-6-isothiocyanatohexane, isothiocyanatocarbonyl isocyanate and 1-isocyanato-4-isothiocyanatocyclohexane; aromatic compounds such as 1-isocyanato-4-isothiocyanatobenzene and 4-methyl-3-isocyanato-1-isothiocyanatobenzene; heterocyclic compounds such as 2-isocyanato-4,6-diisothiocyanato-1,3,5-triazine; and compounds containing one or more sulfur atom in addition to an isothiocyanato group, such as 4-isocyanato-4'-isothiocyanatodiphenyl sulfide and 2-isocyanato-2'-isothiocyanatodiethyl disulfide.

Also usable are their halogen-substituted derivatives such as chlorine-substituted derivatives and bromine-substituted derivatives, alkyl-substituted derivatives, alkoxy-substituted derivatives, nitrosubstituted derivatives, prepolymer-type derivatives modified with polyhydric alcohols, carbodiimidemodified derivatives, urea-modified derivatives, biuret-modified derivatives, dimerized reaction products, trimerized reaction products, and the like. These cyanate compounds can be used either singly or in combination.

Each of these cyanate compounds and the mercapto compound represented by the formula (1) are used at an (NCO+NCS)/SH molar ratio generally in a range of 0.5–3.0, preferably 0.5–1.5.

The plastic lens according to this invention uses as a material an S-alkyl thiocarbamate resin or dithiourethane resin which predominantly contains S-alkyl thiocarbamate bonds, each formed of an isocyanato group and a mercapto group or a dithiourethane bonds, each formed of an isothiocyanato group and a mercapto group and, depending upon the application purpose, may additionally contain allophanate bonds, urea bonds, thiourea bonds, biuret bonds and/or the like. Preferred results can be brought about in many instances, for example, when isocyanate groups are reacted to S-alkyl thiocarbamate bonds or isothiocyanate groups are reacted to dithiourethane bonds to increase the crosslink density. In such a case, the reaction temperature is raised to a high level, i.e., 100° C. or higher and an isocyanate or isothiocyanate component is used in a large amount. As an alternative, an amine or the like can be used as a portion of the isocyanate or isothiocyanate to incorporate urea bonds or biuret bonds. Care must, however, be exercised especially in coloration when a non-mercapto compound reactive with an isocyanate or isothiocyanate compound is used as described above.

Depending on the application purpose as in conventional forming processes, it is also possible to add various materials such as internal mold releasing agents, chain extenders, crosslinking agents, light stabilizers, ultraviolet absorbers, antioxidants, oil-soluble dyes and fillers.

To regulate the reaction velocity to a desired level, a known reaction catalyst employed in the production of polyurethane can also be added as needed.

In general, the lens of this invention can be obtained by casting polymerization. Described specifically, the cyanate compound and the mercapto compound represented by the formula (1) are mixed and, after degasifying the resultant liquid mixture by a suitable method as needed, the liquid mixture is cast in a mold. While gradually raising the temperature of the liquid mixture, the above compounds are polymerized. Although the polymerization temperature and time vary depending on the composition of the monomers and the kinds and amounts of additives, heating of the liquid mixture is generally started from 20° C. or so and the liquid mixture is heated to about 120° C. over 8–24 hours. To facilitate the releasability after the polymerization, known mold-releasing treatment can be applied to the mold.

The sulfur-containing urethane resin according to this invention, which has been obtained as described above, is free of unpleasant feeling due to the odor of sulfur upon handling the monomers and also of unpleasant feeling due to the odor of sulfur upon post working. From the standpoint of physical properties and characteristics, the above sulfur-containing urethane resin has the excellent features that it has low dispersion characteristics and high refractive index, is excellent in heat resistance, is colorless, transparent and lightweight, and superb in weatherability, impact resistance and the like. It is therefore suitable as a material for optical elements such as eyeglass lenses or camera lenses or as a material for a grazing material, coating formulation or adhesive.

Describing further, the use of the mercapto compound in the present invention makes it possible to obtain a sulfur-containing resin having less odor than the use of 1,2,3-trimercaptopropane. Compared with the use of a similar compound, namely, 1,2-[(2-mercaptoethyl)thio]-3-mercaptopropane or 1,2,3-tris[(2mercaptoethyl)thio]-propane, the mercapto compound of this invention can provide a sulfur-containing urethane resin having better heat resistance when reacted with the same isocyanate compound.

The lens, which uses the sulfur-containing urethane resin of this invention as a material, can be subjected to further physical or chemical treatment such as surface polishing, antistatic treatment, hard coating, non-reflective coating, dyeing or photochromic treatment, as needed, in order to prevent reflection, impart high hardness, improve its abrasion resistance, improve its chemical resistance, impart anti-mist property or impart fashionability.

The present invention will hereinafter be described specifically by the following examples and comparative examples.

EXAMPLES 1

In 50 ml of water, 25.3 g (0.324 mole) of 2-mercaptoethanol and 0.1 g of sodium hydroxide were dissolved into a homogeneous solution. While the internal temperature was maintained at 15° C., 24.0 g (0.324 mole) of glycidol were added dropwise to the solution.

After the completion of the dropwise addition, the reaction mixture was heated to 50° C. at which it was stirred for 1 hour. The reaction mixture was then cooled to room temperature and water was removed under reduced pressure, whereby 50.0 g of a triol having the following formula (3) were obtained as a colorless syrup.

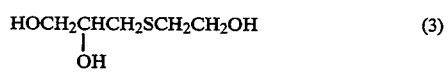

$$\text{HOCH}_2\underset{\underset{\text{OH}}{|}}{\text{CH}}\text{CH}_2\text{SCH}_2\text{CH}_2\text{OH} \qquad (3)$$

The triol was next dissolved in 203 g (2.00 moles) of a 36% aqueous solution of hydrochloric acid, followed by the addition of 92.6 g (1.22 moles) of thiourea. The resulting mixture was then heated under stirring at 110° C. for 6 hours. The reaction mixture was then cooled to room temperature, to which 195 g (2.44 moles) of a 50% aqueous solution of sodium hydroxide were added while the reaction mixture was maintained at 20°–40° C. The mixture so obtained was heated under stirring at 110° C. for 30 minutes.

The reaction mixture was cooled to room temperature and extracted with 100 ml of toluene. The organic layer was washed with 100 ml of a 5% aqueous solution of hydrochloric acid and then washed with 100 ml of water twice. The organic layer was then concentrated under reduced pressure so that 56.1 g (0.281 mole) of 2-(2-mercaptoethylthio)-1,3-dimercaptopropane having the formula (1) were obtained. The reaction product was distilled further at 0.25 mmHg, whereby 45 g of a fraction whose boiling point ranged from 135°–140° C. were obtained.

The results of an elemental analysis and NMR analysis are shown below.

Elemental analysis for $C_5H_{12}S_4$:
Found (%): C, 29.96, H, 6.03, S, 64.01.

Calculated (%): C, 29.97, H, 6.04, S, 64.00.

$^1$H NMR (CDCl$_3$) $\delta_{ppm}$: 1.65–1.85 (3H,m,S$\underline{H}$), 2.70–3.00 (9H,C$\underline{H}$).

$^{13}$C NMR (in CDCl$_3$) $\delta_{ppm}$: 24.9 (—S$\underline{C}$H$_2$), 51.4 (—S$\underline{C}$H).

EXAMPLE 2

In 50 ml of water, 25.3 g (0.324 mole) of 2-mercaptoethanol and 0.1 g of sodium hydroxide were dissolved into a homogeneous solution. While the internal temperature was maintained at 15° C., 30.0 g (0.324 mole) of epichlorohydrin were added dropwise to the solution.

After the completion of the dropwise addition, the reaction mixture was heated to 50° C. at which it was stirred for 1 hour. The reaction mixture was then cooled to room temperature and water was removed under reduced pressure, whereby 56.4 g of a diol having the following formula (4) were obtained as a colorless syrup.

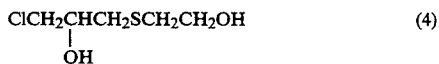

ClCH$_2$CHCH$_2$SCH$_2$CH$_2$OH    (4)
|
OH

The diol was next dissolved in 203 g (2.00 moles) of a 36% aqueous solution of hydrochloric acid, followed by the addition of 92.6 g (1.22 moles) of thiourea. The resulting mixture was then heated under stirring at 110° C. for 6 hours. The reaction mixture was then cooled to room temperature, to which 195 g (2.44 moles) of a 50% aqueous solution of sodium hydroxide were added while the reaction mixture was maintained at 20°–40° C. The mixture so obtained was heated under stirring at 110° C. for 30 minutes.

The reaction mixture was cooled to room temperature and extracted with 100 ml of toluene. The organic layer was washed with 100 ml of a 5% aqueous solution of hydrochloric acid and then washed with 100 ml of water twice. The organic layer was then concentrated under reduced pressure so that 54.3 g (0.272 mole) of 2-(2-mercaptoethylthio)-1,3-dimercaptopropane having the formula (1) were obtained. The reaction product was distilled further at 0.25 mmHg, whereby 44 g of a fraction whose boiling point ranged from 135°–140° C. were obtained.

The results of an elemental analysis and NMR analysis of the thus-obtained compound were the same as those of the compound obtained in Example 1.

EXAMPLE 3

2-(2-Mercaptoethylthio)-1,3-dimercaptopropane (0.33 mole) synthesized in Example 1 and represented by the formula (1) was stirred with 0.5 mole of m-xylylene diisocyanate into a homogeneous mixture. After the mixture was degasified at 3 mmHg for 1 hour, it was cast in a mold formed of a glass mold and a gasket, and then heated and cured. The resin so obtained was colorless and transparent and was excellent in impact resistance. Refractive index, n$_D$: 1.66. Abbe's number, $\nu_D$: 32. Thermal deformation starting temperature: 108° C. The lens was not deformed even when dyed in a dyeing bath of 95° C.

Performance tests of the thus-obtained lens were then conducted. Its refractive index, Abbe's number and weatherability were determined by the following testing methods, respectively.

REFRACTIVE INDEX AND ABBE'S NUMBER

Measured at 20° C. by a Pulfrich refractometer.

Weatherability:

Each lens resin was set in a weather-o-meter equipped with a sunshine carbon arc lamp. Upon an elapsed time of 20 hours, the lens resin was taken out of the weather-o-meter and was compared in color hue with the same lens resin before the test.

The observation results were ranked in accordance with the following standard: no change (A), slight yellowing (B), yellowing (X).

EXTERNAL APPEARANCE

Visually observed.

Odor

Ranked in accordance with the following standard: substantially free of the odor of sulfur (A), slight odor (B), strong odor (C).

Heat resistance

Each test piece was placed under a load of 5 g by using a thermomechanical analyzer (manufactured by Parking-Elmer Inc., U.S.A.). It was heated at a rate of 2.5° C./min so that its thermal deformation starting temperature was measured.

The results are shown in Table 1.

EXAMPLES 4–9

As in Example 3, lenses were fabricated with the compositions in Table 1, respectively. They were evaluated in a similar manner to Example 3. The results are shown in Table 1.

COMPARATIVE EXAMPLE 1

A lens was fabricated as in Example 3 except that 0.33 mole of 1,2,3-trimercaptopropane was used instead of the mercapto compound represented by the formula (1). The lens so obtained was colorless and transparent, and its refractive index (n$_D$) and Abbe's number ($\nu_D$) were 1.65 and 32, respectively. 1,2,3-Trimercaptopropane had strong odor characteristic to sulfur and gave unpleasant feeling upon proportioning the monomers. The thus-fabricated lens also gave off strong odor of sulfur when it was ground.

COMPARATIVE EXAMPLE 2

A lens was fabricated as in Example 3 except that 0.33 mole of 1,2,3-tris[(2-mercaptoethyl)thio]propane was used instead of the mercapto compound represented by the formula (1). 1,2,3-Tris[(2-mercaptoethyl)thio]propane was pale yellow so that the lens so obtained was tinged in a pale yellow color. Its refractive index (n$_D$) and Abbe's number ($\nu_D$) were 1.66 and 32, respectively, but its thermal deformation starting temperature was as low as 83° C.

COMPARATIVE EXAMPLE 3

A lens was fabricated as in Example 3 except that 0.33 mole of 1,2-bis[(2-mercaptoethyl)thio]-3-mercaptopropane was used instead of the mercapto compound represented by the formula (1). The lens so obtained was colorless and transparent, and its refractive index (n$_D$) and Abbe's number ($\nu_D$) were 1.66 and 32, respectively. Its thermal deformation starting temperature was, however, 98° C. so that the lens was deformed when dyed in a dyeing bath of 95° C.

COMPARATIVE EXAMPLE 4

A lens was fabricated as in Example 5 except that 0.33 mole of 1,2-bis[(2-mercaptoethyl)thio]-3-mercaptopropane was used instead of the mercapto compound represented by the formula (1). The lens so obtained was colorless and transparent, and its refractive index ($n_D$) and Abbe's number ($\nu_D$) were 1.70 and 32. Its thermal deformation starting temperature was, however, as low as 76° C.

mixture composed of a mercapto compound represented by the following formula (1):

$$HSCH_2CHCH_2SH \atop | \atop SCH_2CH_2SH \qquad (1)$$

TABLE 1

| | Cyanate compound (mole) | Polythiol (mole) | Refractive index | Abbe's number | Weatherability | Appearance | Odor | Heat resistance (°C.) |
|---|---|---|---|---|---|---|---|---|
| Ex. 3 | m-Xylylene diisocyanate (0.5) | 2-(2-Mercaptoethylthio)-1,3-dimercaptopropane (0.33) | 1.66 | 32 | A | Colorless, transparent | A | 108 |
| Ex. 4 | Isophorone diisocyanate (0.5) | 2-(2-Mercaptoethylthio)-1,3-dimercaptopropane (0.33) | 1.66 | 40 | A | Colorless, transparent | A | |
| Ex. 5 | OCN—CH$_2$SSCH$_2$—NCO (0.5) | 2-(2-Mercaptoethylthio)-1,3-dimercaptopropane (0.33) | 1.70 | 32 | A | Colorless, transparent | A | 98 |
| Ex. 6 | OCN—(CH$_2$)$_6$—NCS (0.5) | 2-(2-Mercaptoethylthio)-1,3-dimercaptopropane (0.33) | 1.67 | — | A | Colorless, transparent | A | |
| Ex. 7 |  (0.5) | 2-(2-Mercaptoethylthio)-1,3-dimercaptopropane (0.33) | 1.72 | — | A | Colorless, transparent | A | |
| Ex. 8 | SCN—(CH$_2$)$_6$—NCS (0.5) | 2-(2-Mercaptoethylthio)-1,3-dimercaptopropane (0.33) | 1.70 | — | A | Colorless, transparent | A | |
| Ex. 9 |  (0.5) | 2-(2-Mercaptoethylthio)-1,3-dimercaptopropane (0.33) | 1.75 | — | A | Colorless, transparent | A | |
| Comp. Ex. 1 | m-Xylylene diisocyanate (0.5) | 1,2,3-Trimercaptopropane (0.33) | 1.65 | 32 | A | Colorless, transparent | C | |
| Comp. Ex. 2 | m-Xylylene diisocyanate (0.5) | 1,2,3-Tris[(2-mercaptoethyl)thio]propane (0.33) | 1.66 | 32 | A | Pale yellow | A | 83 |
| Comp. Ex. 3 | m-Xylylene diisocyanate (0.5) | 1,2-Bis[(2-mercaptoethyl)thio]-3-marcaptopropane (0.33) | 1.66 | 32 | A | Colorless, transparent | A | 98 |
| Comp. Ex. 4 | OCN—CH$_2$SSCH$_2$—NCO (0.5) | 1,2-Bis[(2-mercaptoethyl)thio]-3-mercaptopropane (0.3) | 1.70 | 32 | A | Colorless, transparent | A | 76 |

As is apparent from a comparison between Example 3 and Comparative Examples 2,3 or from a comparison between Example 5 and Comparative Example 4, the mercapto compound according to the present invention can provide a sulfur-containing urethane resin having superior heat resistance to similar compounds when reacted with the same cyanate compound.

What is claimed is:

1. A sulfur-containing urethane resin obtained by reacting a mercapto compound represented by the following formula (1):

$$HSCH_2CHCH_2SH \atop | \atop SCH_2CH_2SH \qquad (1)$$

with at least one cyanate compound selected from the group consisting of polyisocyanate compounds, polyisothiocyanate compounds and isocyanate-group-containing isothiocyanate compounds.

2. The resin of claim 1, which has been obtained by reacting the mercapto compound represented by the formula (1) with at least one cyanate compound selected from the group consisting of polyisocyanate compounds, polyisothiocyanate compounds and isocyanate-group-containing isothiocyanate compounds while using the mercapto compound and the cyanate compound at an (NCO+NCS)/SH molar ratio of 0.5–3.0.

3. A process for the production of a sulfur-containing urethane resin, which comprises heating and curing a mixture composed of a mercapto compound represented by the following formula (1):

and at least one cyanate compound selected from the group consisting of polyisocyanate compounds, polyisothiocyanate compounds and isocyanate-group-containing isothiocyanate compounds.

4. The process of claim 3, wherein a mixture of the mercapto compound represented by the formula (1) and at least one cyanate compound selected from the group consisting of polyisocyanate compounds, poly-isothiocyanate compounds and isocyanate-group-containing isothiocyanate compounds, said mercapto compound and said cyanate compound having been mixed at an (NCO+NCS)/SH molar ratio of 0.5–3.0, is heated and cured.

5. A sulfur-containing urethane resin lens obtained by cast-polymerizing a mercapto compound represented by the following formula (1):

$$HSCH_2CHCH_2SH \atop | \atop SCH_2CH_2SH \qquad (1)$$

and at least one cyanate compound selected from the group consisting of polyisocyanate compounds, polyisothiocyanate compounds and isocyanate-group-containing isothiocyanate compounds.

6. The lens of claim 5, wherein said lens has been obtained by cast-polymerizing the mercapto compound represented by the formula (1) and at least one cyanate compound selected from the group consisting of polyisocyanate compounds, polyisothiocyanate compounds and isocyanate-group-containing isothiocyanate compounds while using the mercapto compound and the cyanate compound at an (NCO+NCS)/SH molar ratio of 0.5–3.0.

7. A process for the fabrication of a sulfur-containing urethane resin lens, which comprises cast-polymerizing a mercapto compound represented by the following formula (1):

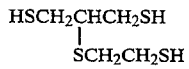
(1)

and at least one cyanate compound selected from the group consisting of polyisocyanate compounds, polyisothiocyanate compounds and isocyanate-group-containing isothiocyanate compounds.

8. The process of claim 7, wherein the mercapto compound represented by the formula (1) and at least one cyanate compound selected from the group consisting of polyisocyanate compounds, polyisothiocyanate compounds and isocyanate-group-containing isothiocyanate compounds are cast-polymerized while using the mercapto compound and the cyanate compound at an (NCO+NCS)/SH molar ratio of 0.5–3.0.

* * * * *